(12) United States Patent
Bailin et al.

(10) Patent No.: US 7,120,491 B1
(45) Date of Patent: Oct. 10, 2006

(54) IMPLANTABLE CARDIOVERSION DEVICE WITH A SELF-ADJUSTING THRESHOLD FOR THERAPY SELECTION

(75) Inventors: Steven Bailin, Urbandale, IA (US); Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 502 days.

(21) Appl. No.: 10/387,651

(22) Filed: Mar. 12, 2003

(51) Int. Cl.
*A61N 1/362* (2006.01)

(52) U.S. Cl. .................................................. 607/5
(58) Field of Classification Search ............ 607/1–156
See application file for complete search history.

(56) References Cited

U.S. PATENT DOCUMENTS

| 4,712,555 | A |  | 12/1987 | Thornander et al. .. 128/419 PG |
| 4,788,980 | A |  | 12/1988 | Mann et al. ............ 128/419 PG |
| 4,809,697 | A |  | 3/1989 | Causey, III et al. ... 128/419 PT |
| 4,940,052 | A |  | 7/1990 | Mann et al. ........... 128/419 PG |
| 4,944,298 | A |  | 7/1990 | Sholder ................. 128/419 PG |
| 4,944,299 | A |  | 7/1990 | Silvian ................... 128/419 PG |
| 5,240,009 | A |  | 8/1993 | Williams ..................... 128/702 |
| 5,718,242 | A | * | 2/1998 | McClure et al. ............ 600/515 |
| 5,779,645 | A |  | 7/1998 | Olson et al. ................. 600/518 |
| 5,882,352 | A | * | 3/1999 | Duncan et al. ................. 607/4 |
| 6,445,949 | B1 |  | 9/2002 | Kroll .............................. 607/4 |

* cited by examiner

*Primary Examiner*—Scott M. Getzow

(57) ABSTRACT

In an implantable cardioversion device, the condition of the patient's heart is determined from an intrinsic ventricular parameter, such as the ventricular rate, and therapy is provided with a pulse generator, including, for instance, antitachycardia pacing therapy or defibrillation shocks. Initially, the conditions, i.e., ventricular tachycardia or fibrillation, are determined using predetermined values for a set of thresholds defining the various conditions. Thereafter, the thresholds are changed by increasing or decreasing the therapy thresholds from the predetermined values based on the morphology of the sensed ventricular signals.

39 Claims, 8 Drawing Sheets

| VENTRICULAR RATE BPM | INTERVAL MS | POSSIBLE DIAGNOSIS VF | AF | VT | NSR |
|---|---|---|---|---|---|
| 500 | 120 | X | | | |
| | 140 | X | | | |
| | 160 | X | | | |
| | 180 | X | | | |
| 300 | 200 | X | | | |
| | 220 | X | | | |
| | 240 | X | | | |
| | 260 | X | X | | |
| | 280 | X | X | X | |
| 200 | 300 | X | X | X | |
| | 320 | X | X | X | |
| | 340 | X | X | X | |
| | 360 | X | X | X | |
| | 380 | | X | X | |
| 150 | 400 | | X | X | |
| | 420 | | X | X | |
| | 440 | | X | X | |
| | 460 | | X | X | X |
| | 480 | | X | X | X |
| | 500 | | X | X | X |
| 120 | 520 | | | | X |
| | 540 | | | | X |
| | 560 | | | | X |
| | 580 | | | | X |
| 100 | 600 | | | | X |
| | 620 | | | | X |
| | 640 | | | | X |

FIG. 4

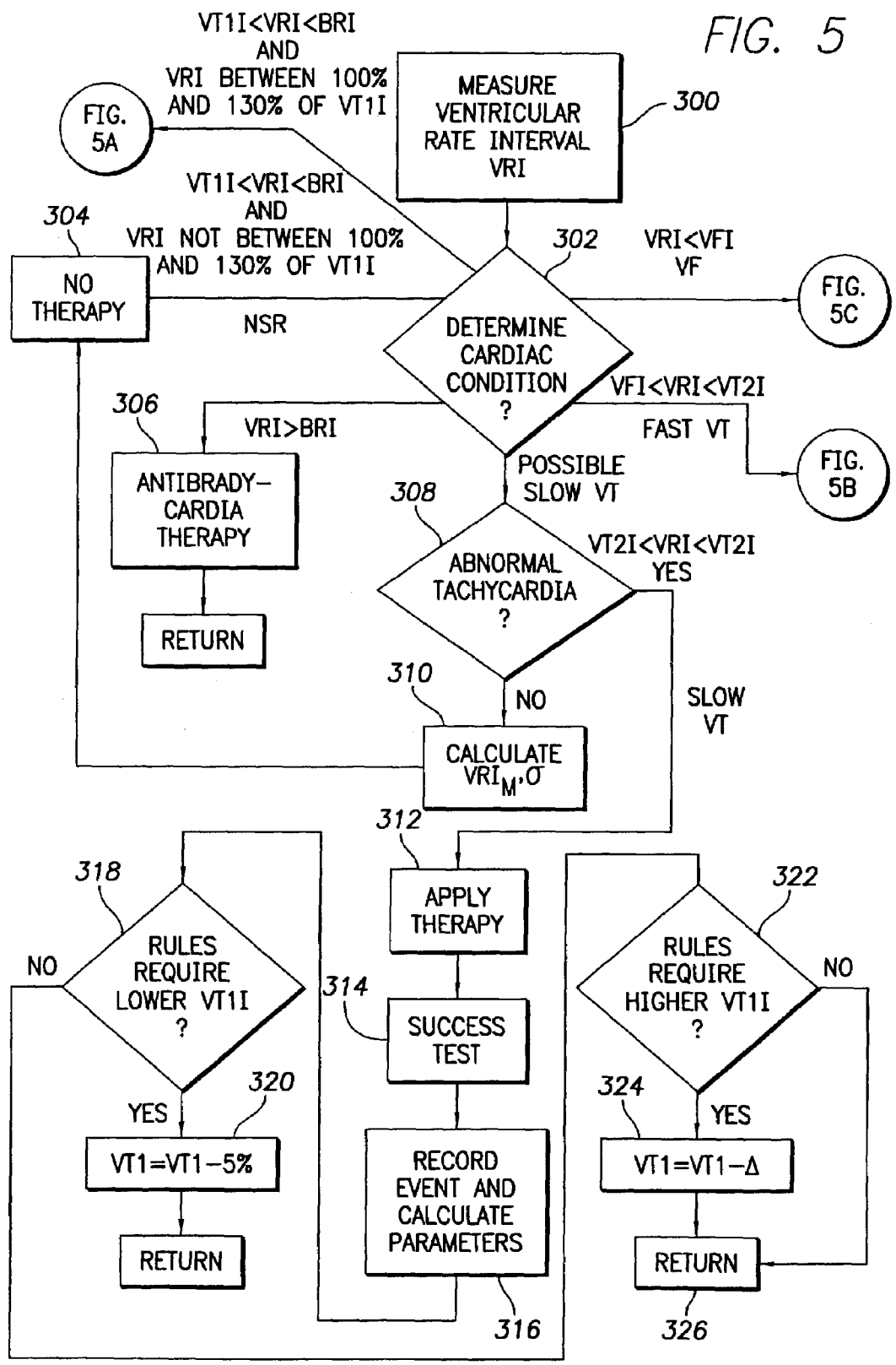

IMPLANTABLE CARDIOVERSION DEVICE WITH A SELF-ADJUSTING THRESHOLD FOR THERAPY SELECTION

FIELD OF THE INVENTION

This invention pertains to implantable medical devices which sense a dangerous cardiac arrhythmia and, in response, provide therapy to the patient's heart to revert it to a normal sinus rhythm. More particularly, the invention pertains to an implantable cardioverter/defibrillator (ICD) including a sensor for sensing intrinsic cardiac activity and a cardioverter/defibrillator to provide various types of antiarrhythmic therapy dependent upon the condition of the heart as indicated by the sensor. The ICD can automatically and dynamically adjust the thresholds which define the various arrhythmic zone therapy zones.

BACKGROUND OF THE INVENTION

As used herein, the term "arrhythmia" refers to any abnormal heart rhythm that may be dangerous to the patient and specifically includes fibrillation, tachycardias, supraventricular tachycardias (SVT), ventricular tachycardias (VT), ventricular fibrillation and flutter (VF), and bradycardia. As further used herein, the term "therapy" refers to any means used by the ICD to restore normal heart rhythm such as defibrillation, cardioversion, antitachycardia pacing (ATP), antibradycardia therapy and drug infusion. The disclosed invention has application to ICDs which treat tachyarrhythmias (abnormally high heart rates).

It has been common practice to monitor the heart rate, or more commonly the ventricular rate, of a patient and classify the cardiac condition of the patient based on this heart rate. For example, tachyarrhythmia may be defined as any rate in a range above a designated threshold VT1. This range is then divided into ventricular tachycardia and ventricular fibrillation (and flutter) zones. The ventricular tachycardia zone may be further divided into slow ventricular tachycardia and fast ventricular tachycardia zones.

However, using heart rate as the sole criterion to classify the cardiac condition of patient is problematic. Many physically active patients have heart rates during exercise that overlap with their tachycardia rates. Other patients exhibit supraventricular tachycardias, the rates of which overlap with rates of tachycardias of ventricular origin. These supraventricular tachycardias are often well tolerated and require no intervention.

When physicians classify an intracardiac rhythm, they typically examine the morphology of the electrocardiogram in addition to the heart rate. The shape of an intracardiac complex holds information on the origin and sequence of the heart's electrical activity. A normal intracardiac complex traverses the AV node and is conducted by specialized cardiac tissue throughout the ventricles. This results in a distinctive complex morphology. A tachycardia of ventricular origin often has a different morphology due to its ectopic origin and conductance through cardiac muscle tissue.

As such, in addition to monitoring heart rate, ICDs are capable of performing morphology discrimination to classify the cardiac condition of the patient. A template based on the morphology of a "known" signal is stored in the ICD. The "known" signal can be, for example, a signal collected during a period where a patient is known to exhibit a normal sinus rhythm. By comparing the morphology characteristics (number, amplitude, sequence and polarity of waveform peaks, as well as the area of the peaks) of an arrhythmia to the template, the ICD can calculate the match between the waveforms. For a complete description of morphology discrimination, refer to U.S. Pat. No. 5,240,009 to Williams, entitled "Medical Device with Morphology Discrimination" and to U.S. Pat. No. 5,779,645 to Olson et al., entitled "System and Method for Waveform Morphology Comparison," which patents are hereby incorporated by reference.

Once it is determined that a patient suffers from one of these cardiac conditions, the ICD is programmed to provide a corresponding therapy. Typically, ventricular tachycardia is treated with a therapy consisting of low-energy pacing pulses designed to capture the ventricle. This therapy is referred to as AntiTachycardia Pacing therapy (ATP). Ventricular fibrillation, on the other hand, is treated more aggressively with high energy shocks. The ICD is programmed with parameters for various types of therapies and the rates defining the therapy zones corresponding to the respective therapies.

Over the years, the number of programmable parameters has been increasing steadily. A modern ICD has up to 200 or more programmable parameters. A major challenge for both the ICD manufacturer and the clinician is to select proper values for these parameters. While the manufacturer may provide nominal or default values for the parameters, these nominal values may not be proper for all patients and it is up to the clinician to change them using statistical information and his personal experience.

For example, approximately 7% of ICD patients exhibit ventricular tachycardia that is typically too slow to be detected by conventional rate cutoffs. Thus, the ICD may fail to discriminate between normal sinus rhythm and slow ventricular tachycardia. However, changing and adapting the parameters have proven to be difficult and it has been found that most clinicians leave the majority of the parameters at their nominal values.

Furthermore, some of the parameters, including the thresholds defining the antitachycardia therapies described above, should be changed periodically to conform to the changing condition of the patient.

It is, hence, desirable to provide an ICD capable of selecting or adjusting some of its parameters automatically so that the clinician does not have to set them on implantation or adjust them each time the condition of the heart changes. More importantly, it would be advantageous to provide an ICD which can adjust some of its parameters adaptively, quickly and efficiently setting them at their optimal levels, and resetting or re-adjusting them automatically as the condition of the patient changes.

The present invention addresses the problem of automatically and dynamically adjusting the thresholds which define the various tachyarrhythmia therapy zones.

SUMMARY OF THE INVENTION

In its broadest sense, the present invention pertains to an ICD which includes a timing and control circuit adapted to classify the condition of a patient as being one of certain preselected types of cardiac conditions based essentially, but not necessarily exclusively, upon the heart rate. The ICD further includes a circuit for selecting and setting thresholds which define the therapy zones corresponding to cardiac conditions. These thresholds are adaptively changed to conform to the individual characteristics and requirements of the patient. In this manner, the ICD can be programmed with initial thresholds, selected either by the manufacturer or the clinician, which are based on statistical information from other patients, etc. These thresholds are then automatically adjusted by the ICD over time. Thus, the clinician does not need to change the default settings or reprogram the ICD during a subsequent visit if the condition of the patient changes.

More particularly, the present invention contemplates an ICD comprising a sense amplifier that generates a sense signal indicative of intrinsic events in the ventricle; a control and timing circuit which generates control signals responsive to the sense signal to define a tachyarrhythmia therapy; a pulse generator that receives the control signals and generates corresponding output signals delivered to the patient's heart; and a threshold setting circuit for setting the thresholds which define the various zones characteristic of specific cardiac conditions associated with tachyarrhythmia. Importantly, a morphology discrimination circuit is provided to analyze a detected ventricular tachycardia signal. This information is used to determine whether a particular threshold should be changed and, if so, whether the particular threshold should be raised or lowered. The morphology discrimination circuit may be implemented to determine whether a particular threshold should be raised or lowered. Additional criteria may also be used to determine if a threshold should be adjusted. Preferably, the ICD is also provided with a memory for storing various programming and operational parameters, as well as a set of rules for setting each threshold.

BRIEF DESCRIPTION OF THE DRAWINGS

The above and other aspects, features and advantages of the present invention will be more apparent from the following more particular description thereof, presented in conjunction with the following drawings wherein:

FIG. 4 shows actual cardiac conditions with overlapping ventricular rates or intervals.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

As indicated above, the present invention may be used with various types of implantable medical devices, including an ICD. To better understand the invention, it will first be helpful to have an understanding of the basic functions performed by an exemplary implantable medical device with which the invention is used, e.g., an ICD. To that end, reference is first made to FIG. 1, where there is shown a simplified functional block diagram of an ICD 20. It should also be noted that, in some instances, the functions of an ICD and a pacemaker may be combined within the same medical device. However, for purposes of the explanations that follow, only an ICD is described herein.

Figure 1:
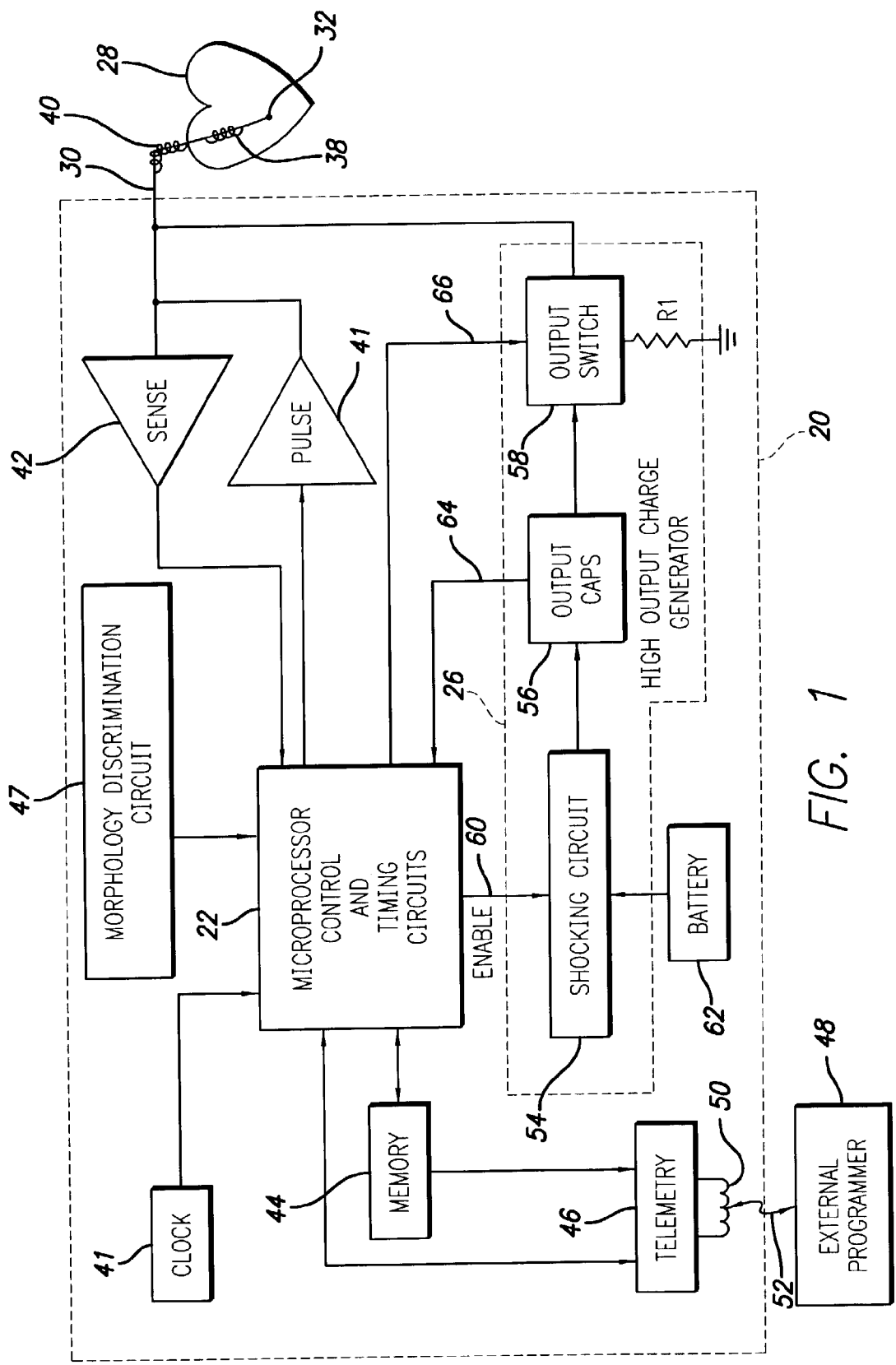
FIG. 1 shows a simplified functional block diagram of an exemplary ICD representing one type of implantable medical device with which the present invention may be used.

It is the primary function of an ICD to sense an arrhythmia and attempt to terminate it automatically by applying an appropriate electrical therapy to the heart. To this end, ICD 20, as shown in the functional block diagram of FIG. 1, includes a microprocessor-based control and timing circuit 22 (hereafter "control/timing" circuit 22) that controls an output charge generator 26. The output charge generator 26 receives power from battery 62 and generates electrical stimulation pulses of moderate or high energy (cardioversion or defibrillation pulses), e.g., electrical pulses having energies of from 1 to 10 joules (moderate) or 11 to 40 joules (high), as controlled by the control/timing circuit 22. Such moderate or high energy pulses are applied to the patient's heart 28 through at least one lead 30 which is coupled to suitable implanted electrodes 38 and 40, positioned in the heart 28. While only one lead and two electrodes are shown in FIG. 1, it is to be understood that additional defibrillation leads and electrodes may be used as desired or needed in order to efficiently and effectively apply the shock treatment generated by the output charge generator 26 to the heart 28.

Alternatively, for less severe tachyarrhythmias such as ventricular tachycardia, pacing pulses may be applied by a pulse generator 41 in response to commands from control/timing circuit 22.

The ICD 20 also includes a sense amplifier 42 that is coupled to sensing lead 30 and electrode 32. Sense amplifier 42 senses the activity of the heart 28 by detecting certain electrical signals sensed through the electrode 32. As is known in the art, R-waves occur upon the depolarization, and hence contraction, of ventricular tissue; and P-waves occur upon the depolarization, and hence contraction, of atrial tissue. Thus, by sensing R-waves and/or P-waves through the sense amplifier 42, and providing such sensed signals to the control/timing circuit 22, the control/timing circuit 22 is able to make a determination as to the rate and regularity of the patient's heart beat. Such information, in turn, allows the control/timing circuit 22 to determine whether the heart 28 is experiencing an arrhythmia.

A morphology discrimination circuit 47 is coupled to the control/timing circuit 22. The morphology discrimination circuit 47 extracts peak amplitude, peak polarity and peak width information from output of the sense amplifier 42. Thus, in addition to the rate and regularity of the patient's heart beat, the control/timing circuit 22 uses the morphology information to discriminate arrhythmias from normal sinus rhythm.

The control/timing circuit 22 further has a memory circuit 44 coupled thereto wherein the operating parameters used by the control/timing circuit 22 are stored. Such operating parameters define, for example, the amplitude of each shock energy pulse to be delivered to heart 28 within each tier of therapy, and its duration. The memory 44 may take many forms, and may be subdivided into as many different memory blocks or sections (addresses) as needed to store desired data and control information. A feature of the present invention, in some embodiments thereof, is the ability to sense and store a relatively large amount of data as a data record, which data record may then be used to guide the operation of the device, i.e., the present operating mode of the device may be dependent, at least in part, on past performance data.

Advantageously, the operating parameters of the ICD 20 may be non-invasively programmed into the memory 44 through a telemetry circuit 46, which is in telecommunications contact with an external programmer 48 by way of a suitable coupling coil 50. The coupling coil 50 may serve as an antenna for establishing a radio frequency (RF) communication link 52 with the external programmer 48 or the coil 50 may serve as a means for inductively coupling data between the telemetry circuit 46 and the external programmer 48, as is known in the art. See, e.g., U.S. Pat. No. 4,809,697 to Causey, III et al. and U.S. Pat. No. 4,944,299 to Silvian, incorporated herein by reference. Further, the telemetry circuit 46 advantageously allows status information relating to the operation of the ICD 20, as contained in the control/timing circuit 22 or memory 44, to be sent to the external programmer 48 through the established link 52.

The control/timing circuit 22 includes appropriate processing and logic circuits for analyzing the output of the sense amplifier 42 and determining if such signals indicate the presence of an arrhythmia. Typically, the control/timing circuit 22 is based on a microprocessor, or similar processing circuit, which is capable of processing or monitoring input signals (data) in a prescribed manner, e.g., as controlled by program code stored in a designated area or block of the memory 44. The details of the design and operation of the control/timing circuit 22 are not critical to the present invention. Rather, any suitable control/timing circuit 22 may be used that carries out the functions described herein. The use, design, and operation of microprocessor-based control circuits to perform timing and data analysis functions is known in the art. The telemetry or communications circuit 46 may be of conventional design, such as is described in U.S. Pat. No. 4,944,299, or as is otherwise known in the art.

Representative of the types of control systems that may be used with the invention is the microprocessor-based control system described in U.S. Pat. No. 4,940,052, entitled "Microprocessor Controlled Rate-Responsive Pacemaker Having Automatic Rate Response Threshold Adjustment". Reference is also made to U.S. Pat. Nos. 4,712,555 and 4,944,298, wherein a state-machine type of operation for a pacemaker is described and U.S. Pat. No. 4,788,980, wherein the various timing intervals used within the pacemaker and their inter-relationships are more thoroughly described. The '052, '555, '298 and '980 patents are incorporated herein by reference.

As previously mentioned, an important feature of the present invention is that it is able to adapt itself automatically to the individual characteristics of the patient thereby eliminating the lengthy, uncomfortable testing period required to determine and set the various thresholds that have been required with standard ICD implantations until now. The invention is best understood by describing its normal mode of operation.

Figure 2:
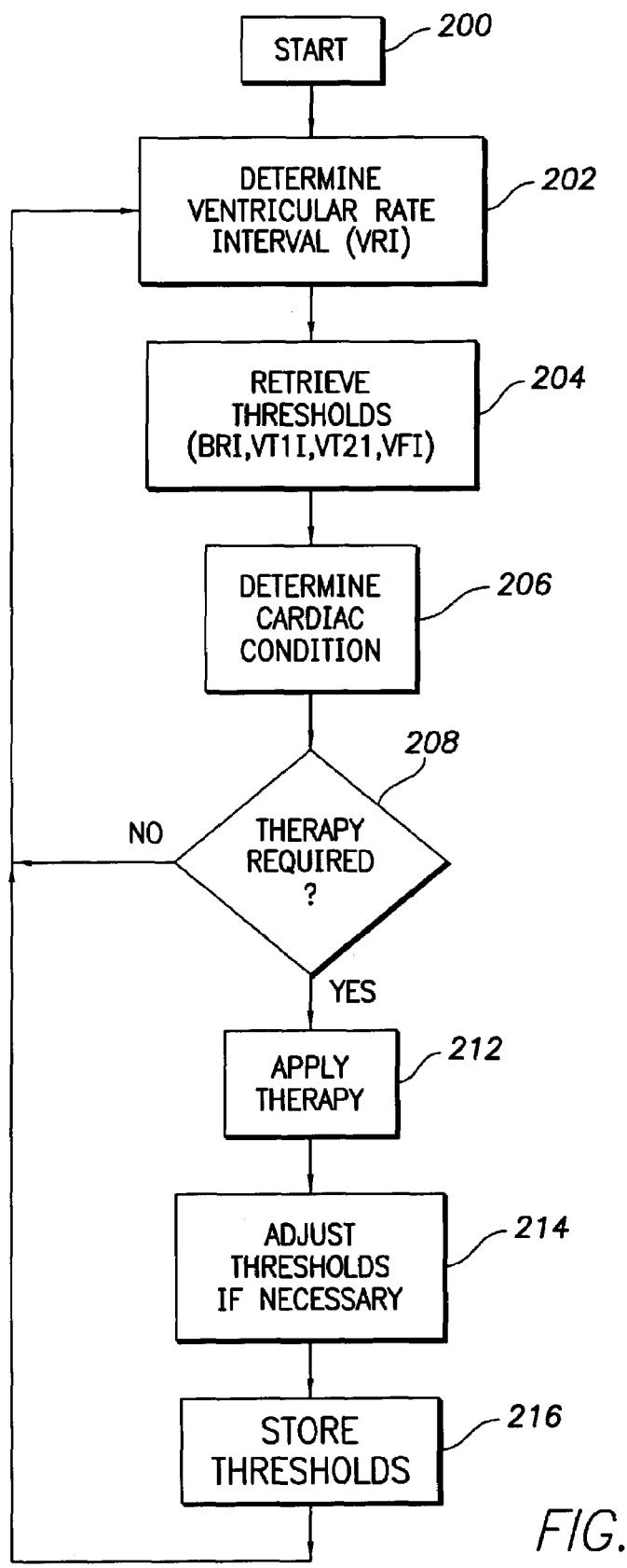
FIG. 2 shows a flow chart for the operation of the exemplary ICD in accordance with this invention.

Referring now to FIG. 2, after implantation, operation of the ICD 20 begins at START block 200. In block 202, the ICD determines the ventricular rate interval (VRI) corresponding to the current ventricular rate (VR) of the intrinsic ventricular beat of the heart using, for example, information received from sense amplifier 42. In block 204, the control/timing circuit 22 retrieves from memory 44 the current interval thresholds which define the various cardiac zones. Initially, these interval thresholds are either preprogrammed by the manufacturer or are set by the clinician after implantation, using the patient's age, health, prior cardiac history, and present condition as criteria.

Figure 3:
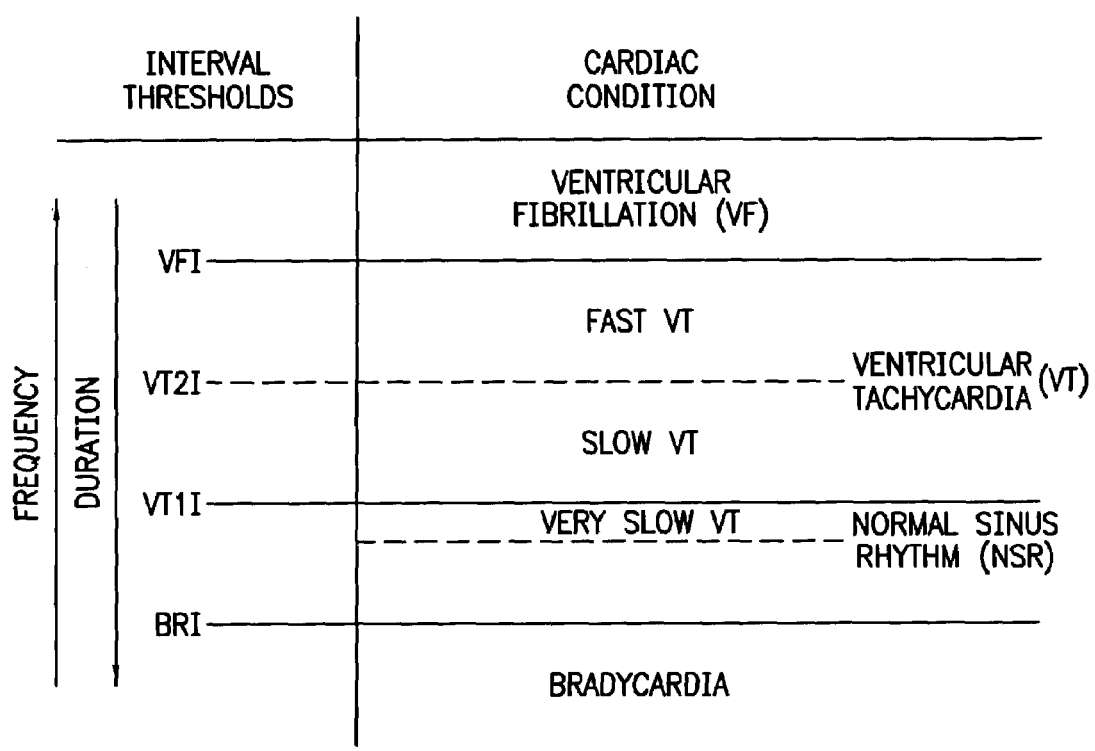
FIG. 3 shows graphically the zones for various cardiac rhythms used by the exemplary ICD.

FIG. 3 shows a typical cardiac condition classified into zones by heart rate intervals stored in memory 44. The heart rate increases as the time interval between heart beats decreases. Accordingly, while FIG. 3 shows zones which increase upwards in frequency ranges, the designated interval thresholds, i.e., BRI, VT1I, VT2I, and VFI decrease in time duration as the corresponding frequency ranges increase. In a preferred implementation of the present invention, the thresholds used correspond to the intervals between heart beats since hardware for measuring intervals, i.e., time durations, is generally easier to implement than hardware that measures rates, i.e., frequencies. However, implementations that determine heart rates and therefore use rate thresholds are considered to be alternative implementations of the present invention.

A ventricular rate interval (VRI) greater than the bradycardia interval threshold BRI (i.e., below a bradycardia frequency threshold) is classified as bradycardia. Between interval thresholds BRI and VT1I (the interval threshold for a slow ventricular tachycardia), the cardiac rate is at a normal sinus rhythm. Between interval thresholds VT1I and VFI (the interval threshold for indicating ventricular fibrillation), the heart condition is classified as ventricular tachycardia (VT). Frequently this condition is partitioned into two zones, slow VT and fast VT, by an interval threshold VT2I, with a different antitachyarrhythmic pacing regimen or other therapy being applied for each zone. The two therapies are referred to herein as ATP1 and ATP2, respectively. When the ventricular rate interval (VRI) is less than the VFI interval threshold (i.e., when the heart rate exceeds a ventricular fibrillation rate), the cardiac condition is classified as ventricular fibrillation or flutter which is normally treated by shock therapy. The interval thresholds BRI, VT1I, VT2I and VFI are determined for each patient by the clinician, as described above, immediately following implantation or, alternatively, by initial use of standard default settings. It should be understood that the scheme in FIG. 3 may be used to classify patient cardiac conditions and to determine what therapy (if any) should be applied to the patient for each condition. Other criteria may refine this determination, which is beyond the scope of this application. A discussion of some of these criteria is found in "IMPLANTABLE CARDIOVERTER DEFIBRILLATOR THERAPY" edited by Mark W. Kroll, Ph.D. and Michael H. Lehmann, M.D., Kluwer Academic Publishers, 1996, pp. 305–307.

FIG. 4 shows a table indicating measured ranges for the ventricular rates and time intervals (which are the inverse of the ventricular rates) corresponding to various cardiac conditions. As can be seen from this figure, there is considerable overlap between ventricular rates corresponding to VF (ventricular fibrillation), AF (atrial fibrillation), VT (ventricular tachycardia) and NSR (normal sinus rhythm). Accordingly, ventricular rate by itself may not be sufficient for a prognosis if the interval thresholds of FIG. 3 are maintained at predetermined levels.

What is contemplated in the present invention is the dynamic adjustment of the interval thresholds (or conversely the corresponding frequency thresholds) by the ICD 20, which can be accomplished as follows. Initially, the values of the various interval thresholds (whether preset, or programmed by the clinician) are stored in memory 44. Referring again to FIG. 2, after the current ventricular rate interval (VRI) is determined in block 202, the initial interval thresholds are retrieved in block 204 from memory 44. In block 206, the cardiac condition of the patient is determined using the current value of the ventricular rate interval (VRI) and the condition classification scheme of FIG. 3. In block 208, a determination is made as to whether therapy is required. If no therapy is required, then a new value for the ventricular rate interval (VRI) is determined based on the next intrinsic cardiac event.

If the current ventricular rate interval (VRI) is outside the NSR (normal sinus rhythm) zone or if very slow VT is suspected based on morphology discrimination, then, in block 212, a therapy is selected that is appropriate to the applicable classification defined by the zones of FIG. 3. For example, antitachycardia pacing is implemented if very slow VT is suspected. During or after the application of therapy, the interval thresholds are adjusted (if necessary) in block 214 (as discussed below) and the new interval thresholds are stored in block 216. Following the next ventricular rate interval (VRI) determination of block 202, these new interval thresholds are retrieved in block 204 and used for subsequent threshold interval determinations.

Exemplary initial values for the interval thresholds, as well as the upper and lower limits in milliseconds (ms) are set as follows (since the invention pertains to ICDs designed primarily for antitachyarrhythmic therapy, a discussion of the bradycardia interval threshold (BRI) is omitted herein):

| INTERVAL THRESHOLD | INITIAL OR DEFAULT | MINIMUM | MAXIMUM |
|---|---|---|---|
| Very Slow VT | N/A | 500 ms | 650 ms |
| VT1I | 400 ms | 300 ms | 500 ms |
| VT2I | 320 ms | Max{(VFI + 20), 260} ms | Max{(VT1I − 20), 400} ms |
| VFI | 280 ms | 200 ms | 400 ms | wherein VFI refers to the ventricular fibrillation threshold interval, VT1I and VT2I refer to threshold intervals for determining the range of ventricular tachycardia and Max {A, B} refers to an operation for choosing the larger of A and B.

Initially, based on these limits (and perhaps other criteria as set forth above), the control/timing circuit 22 first determines the patient's cardiac condition. More specifically, the control/timing circuit 22 determines the cardiac condition as being bradycardia, normal sinus rhythm, very slow VT, slow VT, fast VT or ventricular fibrillation. Therapy for the various arrhythmia conditions are known in the art, as discussed for example in the above-mentioned textbook "IMPLANTABLE CARDIOVERTER DEFIBRILLATOR THERAPY" and will not be discussed here in detail.

A more detailed description of an exemplary operation of control/timing circuit 22 is shown in FIGS. 5, 5A, 5B, and 5C. Initially, in block 300, the ventricular rate interval (VRI) is measured. Then, in block 302, the current cardiac condition of the patient is determined, preferably using the ventricular rate interval as a criterion, as shown in FIG. 3, and using morphology discrimination. In an exemplary implementation, this determination is done by a software construct, e.g., a series of "IF-THEN-ELSE" statements, a "DO CASE" statement, or the like, which determines the next step to be processed by comparing the measured ventricular rate interval (VRI) to a series of interval thresholds, e.g., BR1, VT1I, VT2I, and VFI.

Figure 5A:
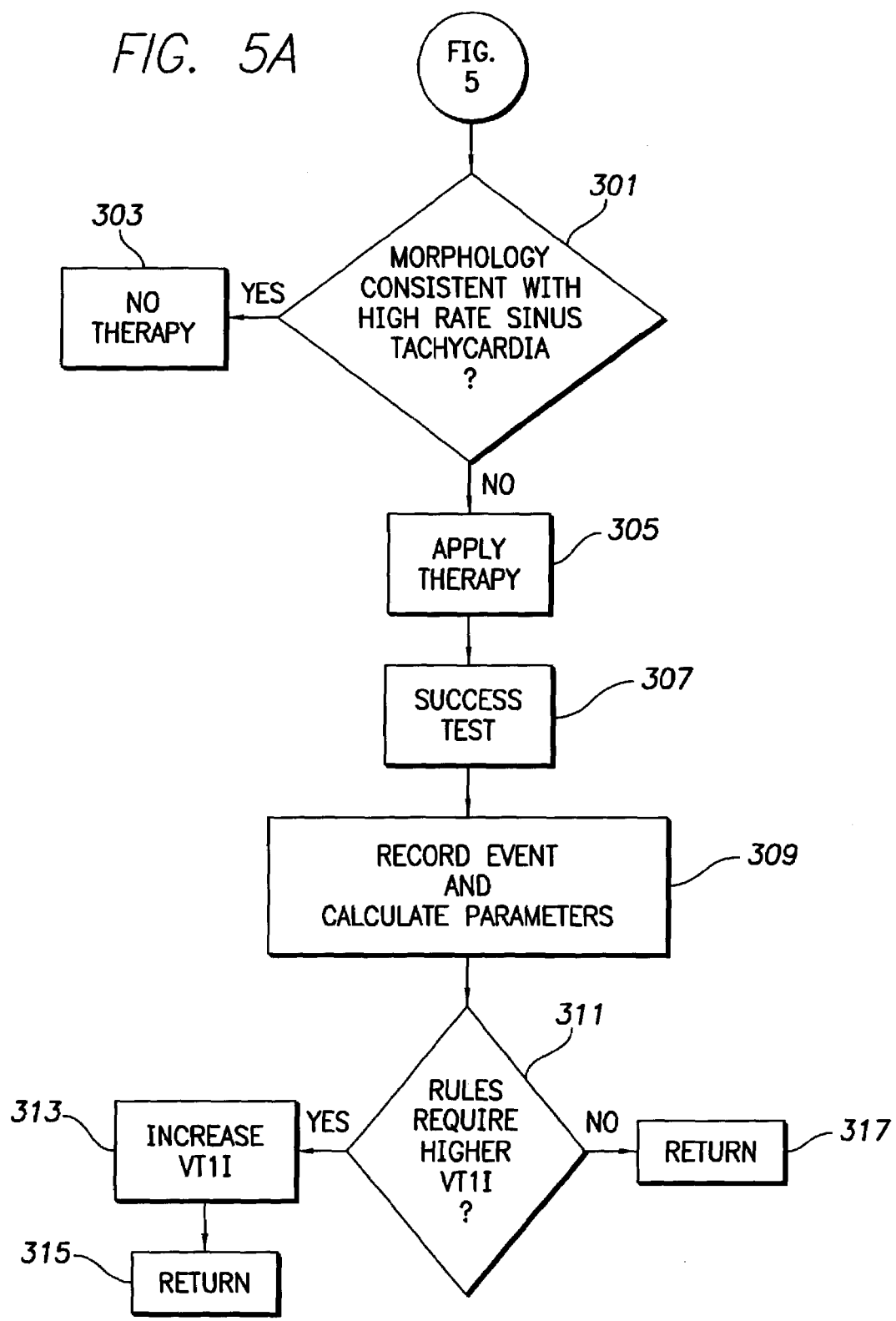
FIGS. 5, 5A, B and C show a detailed flow chart of an exemplary method used by an ICD to dynamically adjust the thresholds defining the therapy zones.
Figure 5B:
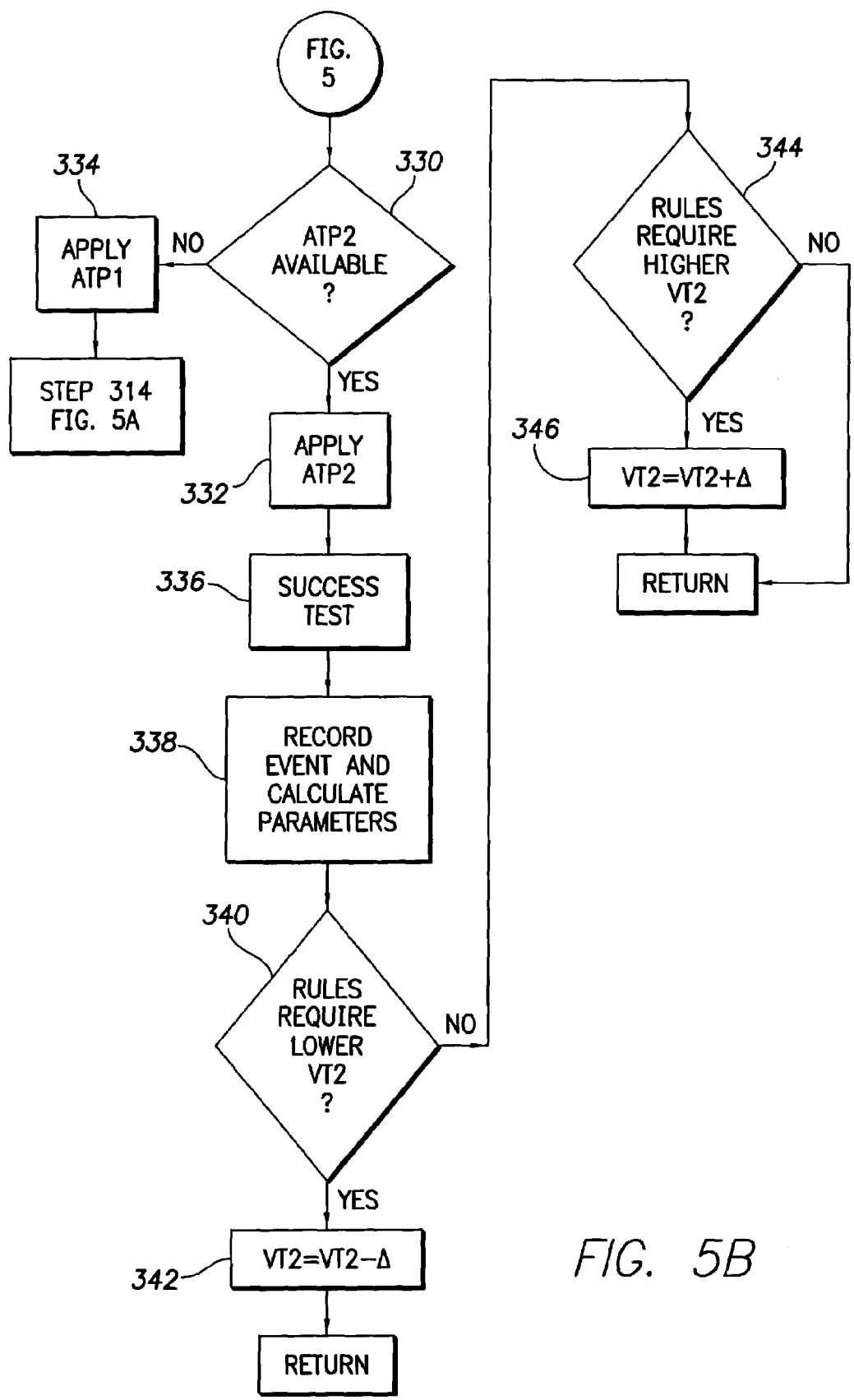
Figure 5C:
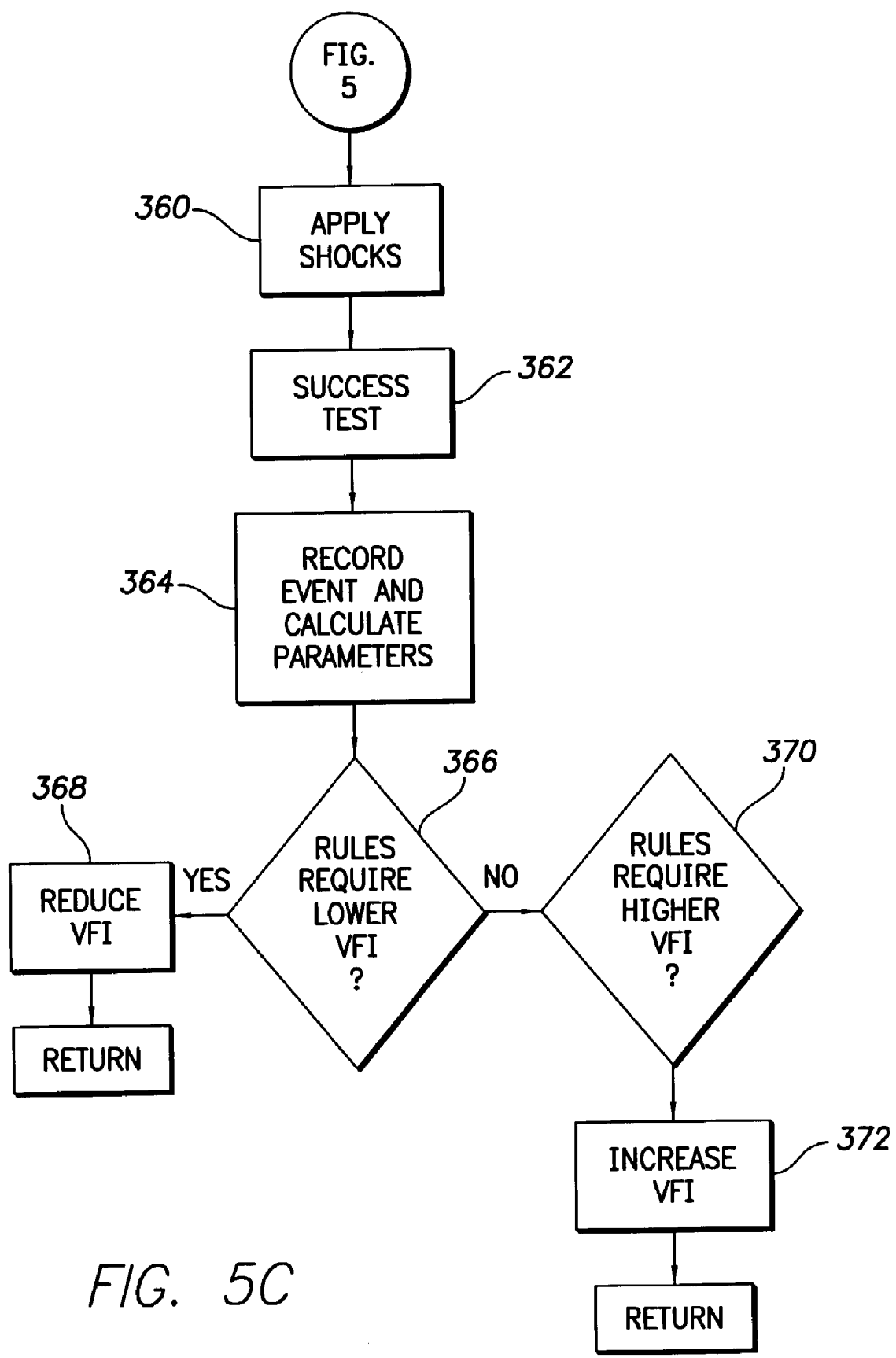

As shown in FIG. 5, if the ventricular rate interval (VRI) is between interval thresholds BRI and VT1I (VT1I<VRI<BRI) and VRI is not between 100% and 130% of VT1I, normal sinus rhythm is indicated at block 304 and no therapy is required. If the ventricular rate interval (VRI) is between interval thresholds BRI and VT1I (VT1I<VRI<BRI) and VRI is between 100% and 130% of VT1I, then a possible very slow VT condition is treated as described in FIG. 5A. If the ventricular rate interval (VRI) is greater than the interval threshold BRI (VRI>BRI), then antibradycardia therapy is applied at block 306. If the ventricular rate interval VRI is between interval thresholds VT2I and VFI (VFI<VRI<VT2I), then a fast ventricular tachycardia (fast VT) condition is treated as described in FIG. 5B. If the ventricular rate interval VRI is less than the interval threshold VFI (VRI<VFI), then a ventricular fibrillation (VF) condition is treated as described in FIG. 5C.

Referring again to FIG. 5, if a ventricular rate interval VRI is between interval thresholds VT1I and VT2I (VT2I<VRI<VT1I), then a slow ventricular tachycardia (slow VT) condition is determined. In block 308, a test is performed to determine or confirm that the detected condition is indeed an abnormal tachycardia, which may require therapy, and not an elevated normal sinus rhythm (ENSR, also referred to as a sinus tachycardia) due, for instance, to exercise. One test for distinguishing slow VT from an elevated normal sinus rhythm (ENSR) is to analyze the onset of the VT condition. For this purpose, in block 308, a baseline or average ventricular rate interval ($VRI_{av}$) is determined (for example, by averaging VRI for the last four beats), and the current value of VRI (i.e., the value which has been determined in block 302 to correspond to slow VT) is compared to this $VRI_{av}$. Slow VT is determined if the current VRI is less than $VRI_{av}$ by greater than a preselected ratio, such as 10%, indicating a fast onset that is characteristic of slow VT rather than ENSR. Conversely, the equivalent determination can be made by looking for an increase in the average ventricular rate. Other means of distinguishing ENSR from slow VT may be used as well.

If it has been determined that the patient's elevated heart rate is based upon an elevated normal sinus rhythm (ENSR), e.g., resulting from exercise, calculations are performed in block 310 to determine the statistics of the ventricular rate interval (VRI), including its mean value $VRI_M$ and its standard deviation $\sigma$. Once these parameters are obtained (preferably in milliseconds), they are used to determine whether the patient is relatively young and fit and to determine how the interval thresholds are adjusted in the following steps of the disclosed invention.

If block 308 does show a slow VT (i.e., an elevated normal sinus rhythm is not shown), then, in block 312, appropriate therapy is applied. In block 314, a test is performed to determine if the therapy applied in block 312 was successful. In block 316, the results of the test from block 314 are logged or recorded in memory 44. These results are tabulated over several abnormal VT events. In addition, several other parameters are also calculated and are used to determine whether the thresholds of FIG. 3 are appropriate. More particularly, block 318 utilizes a set of rules to determine, historically, whether the interval threshold VT1I needs to be adjusted, preferably by a predetermined amount, e.g., 5%. The following is an exemplary set of rules that may be applied in block 318 to determine if the interval threshold VT1I should be decreased and the corresponding frequency threshold increased:

A. $(VRI_M - 4\sigma) > VT1I$, and

B. over 90% of VT1I crossings (i.e., excursions of VRI below VT1I) are not confirmed in block 308 as sudden onset.

Another set of rules for decreasing the threshold interval VT1I is:

C. $(\sigma/VRI_M) > 10\%$, and

D. 90% of the VT1I crossings are rejected by the fast onset criterion of block 308, and E. The ATP1 success rate in the slowest 20% of VT events is less than 50%.

Alternatively, the following set of rules can be used in block 322 to determine if the interval threshold VT1I should be increased and the corresponding frequency threshold decreased:

F. $(VRI_M - 6\sigma) > VT1I$, and

G. The ATP1 success rate in the slowest 20% zone of VT events is over 80% (suggesting very little atrial fibrillation or normal sinus rhythm), and H. 90% of the VT1I crossings are confirmed by the fast onset tests of blocks 308 as being ventricular tachycardia (VT) and not an elevated normal sinus rhythm.

Referring again to FIG. 5, the parameters required by these rules for slow VT are calculated in block 310 and, in block 318, a determination is made using the rules set forth whether the interval threshold VT1I should be lowered. If yes, then, in block 320, the threshold setting circuit 80 decreases the interval threshold VT1I, preferably by a predetermined amount Δ, e.g., 5%. In block 322, the rules above are used to determine if interval threshold VT1I should be increased. If yes, then, in block 324, the interval threshold VT1I is increased, preferably by a predetermined amount Δ, e.g., 5%. If not, then the interval threshold VT1I remains the same (block 326).

As discussed previously, some patients exhibit ventricular tachycardia (VT) that is too slow to be detected by the conventional rate cutoffs. Morphology discrimination can be implemented to verify that a moderate rate is, in fact, a ventricular tachycardia (VT). FIG. 5A depicts the blocks performed if ventricular rate interval (VRI) is between interval thresholds BR1 and VT1I (VT1I<VRI<BRI) and VRI is between 100% and 130% of VT1I, wherein very slow ventricular tachycardia (VT) may be suspected. First, in block 301, morphology discrimination is performed to determine if the QRS complex is consistent with high rate sinus tachycardia. If yes, then elevated normal sinus rhythm is indicated at block 303 and no therapy is required. If no, then ATP1 therapy is applied at block 305. In block 307, a test is performed to determine if the ATP1 therapy applied in block 305 was successful. These results are tabulated over several abnormal VT events. In addition, several other parameters are also calculated and are used to determine whether the thresholds of FIG. 3 are appropriate. More particularly, block 311 utilizes a set of rules to determine, historically, whether the interval threshold VT1I needs to be adjusted, preferably by a predetermined amount, e.g., (VRI$_M$+2σ). In addition to rules F, G, and H, the following set of exemplary rules may be applied in block 311 to determine if the interval threshold VT1I should be increased and the corresponding frequency threshold decreased when very slow VT is suspected:

I. VRI is between 100% and 130% of VT1I, and

J. the morphology of the QRS complex is more consistent with ventricular tachycardia (VT) than an elevated normal sinus rhythm (the morphology of the QRS complex can be compared with a stored template), and K. ATP1 is successful in any of the VT events.

Referring again to FIG. 5A, the parameters required by the rules for very slow VT are calculated in block 309 to determine the statistics of the ventricular rate interval (VRI), including its mean value VRI$_M$ and its standard deviation σ. The mean value VRI$_M$ and its standard deviation σ can be measured during the detection time for at least 10 beats. In block 311, a determination is made using the rules set forth whether the interval threshold VT1I should be increased. If yes, then, in block 313, the interval threshold VT1I is increased, preferably by a predetermined amount Δ such that the interval VT1I is increased to (VRI$_M$+2σ) of the detected intervals. In addition, the ATP1 that is finally successful is also set for use in the very slow VT zone. If the interval threshold VT1I is not to be increased, then the interval threshold VT1I remains the same (block 317).

FIG. 5B depicts the blocks performed if fast VT is detected in block 302 of FIG. 5. First, in block 330, a check is performed to determine if the ICD 20 is configured or capable of performing fast VT therapy (ATP2) as a distinct therapy separate from the ATP1 therapy used for very slow/slow VT. The ICD 20 may be set up so that the clinician is given the choice of either requesting a single or universal therapy, in case of all VTs, or requesting a different, i.e., bifurcated, therapy for very slow/slow and for fast VT.

If ATP2 therapy is available for fast VT, then, in block 332, ATP2 therapy is applied. If ATP2 therapy is not available, then, in block 334, ATP1 therapy is applied, and the process of FIG. 5 is continued with block 314.

In block 336, a test is performed to determine if the ATP2 therapy applied in block 332 was successful. The events are recorded in block 338 into memory 44. In block 338, a set of parameters is also calculated either after every VT episode or on a daily basis. More specifically, the number of times that the ATP1 therapy for very slow/slow VT has been successful in the last N (e.g., 10) very slow/slow VT events, and the number of times ATP2 therapy was successful for the last N fast VT events are determined. The parameters VRI$_M$ and σ (defined above) are also determined.

In block 340, another set of rules determine whether the interval threshold VT2I needs to be changed. The following exemplary rules may be used to determine if the interval threshold VT2I should be decreased and the corresponding frequency threshold increased:

L. No unsuccessful therapy events occurred in the very slow/slow VT zone; and

M. (VRI$_M$+σ) of events with unsuccessful therapy in the fast VT zone is greater than VT2I.

If the rules in block 340 indicate that interval threshold VT2I is too high then, in block 342, the interval threshold VT2I is decreased, preferably by a predetermined amount Δ, e.g., 5%. If not, in block 344, a test is performed to determine if the interval threshold VT2I needs to be increased and the corresponding frequency threshold decreased. The following is a set of exemplary rules which may be used in block 344 to this end:

N. The success rate of ATP2 therapy in the high VT zone is greater than the success rate of ATP1 therapy in the very slow/slow VT zone; and O. The mean interval +σ of successful ATP2 events in the high VT zone is greater than the mean of unsuccessful ATP1 events in the very slow/slow VT zone.

If the rules or conditions N–O are met, the interval threshold VT2I is increased in block 346, preferably by a predetermined amount Δ, e.g., 5%.

Referring now to FIG. 5C, if in block 302, a VF condition is identified, then, in block 360, therapy is applied appropriate to this condition. More particularly, for VF, one or more energy shocks are typically applied.

In block 362, the effectiveness and success of the therapy of block 360 is determined. In block 364, the results of the test of block 362 are recorded in memory 44. The parameters VRI$_M$ and a are also calculated at this time.

In block 366, a set of rules determine whether the interval threshold VFI needs to be lowered and the corresponding frequency raised. A set of exemplary rules for decreasing VFI is as follows:

P. If (VRI$_M$+2σ) of VFI events is less than VFI (over 10 shocks), then reduce VFI to (VRI$_M$+2σ).

Q. If a series of shocks is applied as part of therapy in block 360 and the whole series is unsuccessful, it is assumed that atrial fibrillation (AF) is present and VFI is reduced by 5%.

If the rules indicate that a decrease is necessary, then the interval threshold VFI is decreased in block 368.

If the interval threshold VFI is not required to be decreased then, in block 370, another set of rules is used to determine if the interval threshold VFI needs to be increased. A set of exemplary rules for increasing the interval threshold VFI are as follows:

R. If ($VRI_M+\sigma$) of VFI events is greater than VFI over the last 10 shocks, increase VFI to ($VRI_M+\sigma$).

S. If the ATP2 therapy for fast VT fails when the current VRI is within (i.e., higher than) a percentage (e.g., 10%) of VFI, increase VFI.

If these rules indicate an increase, then, in block 372, the interval threshold VFI is increased, as prescribed by the rules.

In this manner the interval thresholds VT1I, VT2I, VFI are automatically and adaptively adjusted by the ICD 20 for the individual requirements and characteristics of each patient.

While the invention has been described by means of specific embodiments, it is understood that modification and variations could be made thereto by those skilled in the art without departing from the spirit and the scope of the invention. For example, while the patient condition zones have been defined using threshold intervals by measuring and comparing time durations, an equivalent function can be accomplished by using threshold frequencies and measuring and comparing frequencies. Additionally, while flow charts have been described, preferably for implementation by the microprocessor control/timing circuit in a software implementation, portions of the flow charts can also be implemented in hardware blocks separate from the control/timing circuit. For example, separate blocks of hardware may be used to implement portions of the flow charts separate from the control/timing circuit, e.g., a threshold setting circuit, condition detection circuit, and success detector circuit. Such implementations are considered to be within the scope of the present invention. It is therefore to be understood that within the scope of the claims, the invention may be practiced otherwise than as specifically described herein.

What is claimed is:

1. An implantable cardiac stimulation device to provide therapy to a patient's heart, the device comprising:
   a sense amplifier to sense intrinsic signals from the patient's heart and to generate corresponding sense signals;
   a memory circuit to store interval thresholds to determine the type of antiarrhythmic therapy to be applied to the patient's heart for a range of heart rates defined by the interval thresholds;
   a control and timing circuit coupled to the sense amplifier and the memory circuit to generate control signals responsive to the sense signals and the interval thresholds, the control signals to define one of a plurality of antiarrhythmic therapies, wherein the therapy is selected in accordance with the relationship of the sensed heart rate and the interval thresholds;
   an interval threshold adjusting circuit to adjust the interval thresholds stored in the memory circuit in accordance with the response of the patient to the selected antiarrhythmic therapy; and
   a morphology discrimination circuit coupled to the control and timing circuit, at least one of the interval thresholds modified in accordance with a morphology detection applied to the intrinsic signals;
   wherein the interval thresholds define a very slow ventricular tachycardia zone, a slow ventricular tachycardia zone, and a fast ventricular tachycardia zone;
   wherein the at least one of the interval thresholds is an interval threshold VT1I, and wherein the morphology discrimination circuit compares a QRS complex of the intrinsic signals with a stored template to verify the very slow ventricular tachycardia; and
   wherein the QRS complex is compared with the stored template when a ventricular rate interval (VRI) is between 100% and 130% of the interval threshold VT1I.

2. The device of claim 1 wherein the patient's heart beats at a ventricular rate and the interval thresholds are related to the ventricular rate of the patient's heart.

3. The device of claim 1 wherein the interval thresholds define a very slow ventricular tachycardia zone, a slow ventricular tachycardia zone, and a fast ventricular tachycardia zone, and wherein the pulse generator generates less aggressive antitachycardia therapy when the sensed heart rate corresponds to the very slow ventricular tachycardia zone and the slow ventricular tachycardia zone, and generates more aggressive antitachycardia therapy when the sensed heart rate corresponds to the fast ventricular tachycardia zone.

4. An implantable cardiac stimulation device to provide therapy to a patient's heart, the device comprising:
   a sense amplifier to sense intrinsic signals from the patient's heart and to generate corresponding sense signals;
   a memory circuit to store interval thresholds to determine the type of antiarrhythmic therapy to be applied to the patient's heart for a range of heart rates defined by the interval thresholds;
   a control and timing circuit coupled to the sense amplifier and the memory circuit to generate control signals responsive to the sense signals and the interval thresholds, the control signals to define one of a plurality of antiarrhythmic therapies, wherein the therapy is selected in accordance with the relationship of the sensed heart rate and the interval thresholds;
   an interval threshold adjusting circuit to adjust the interval thresholds stored in the memory circuit in accordance with the response of the patient to the selected antiarrhythmic therapy;
   a morphology discrimination circuit coupled to the control and timing circuit, at least one of the interval thresholds modified in accordance with a morphology detection applied to the intrinsic signals; and
   a pulse generator to generate therapeutic pulses to the patient's heart in response to the control signals;
   wherein the therapeutic pulses comprises AntiTachycardia Pacing therapy (ATP), and wherein an interval threshold VT1I is increased when the ATP Is successful.

5. The device of claim 4 wherein the interval threshold VT1I is increased to ($VRI_M+2\sigma$), wherein $VRI_M$ is the mean ventricular rate interval and $\sigma$ is the standard deviation.

6. The device of claim 4 wherein the interval thresholds define ventricular rate ranges, each range corresponding to a cardiac condition, and wherein the control and timing circuit determines the cardiac condition based at least in part on a ventricular rate corresponding to one of the ranges.

7. The device of claim 4 wherein the interval thresholds define a ventricular tachycardia zone and a ventricular fibrillation zone, and wherein the pulse generator generates antitachycardia pacing therapy pulses when the sensed heart rate corresponds to the ventricular tachycardia zone and defibrillation shocks when the sensed heart rate corresponds to the ventricular fibrillation zone.

8. The device of claim 4 wherein the control and timing circuit determines a cardiac condition of the patient based on the ventricular rate and the interval thresholds.

9. The device of claim 4 wherein the interval thresholds define ventricular rate ranges, each range corresponding to a cardiac condition, and wherein the control and timing circuit determines the cardiac condition based at least in part on a ventricular rate corresponding to one of the ranges.

10. The device of claim 9 wherein the control and timing circuit further determines the cardiac condition based on a secondary criteria.

11. The device of claim 10 wherein the secondary criteria comprises sudden onset, wherein the control and timing circuit determines that physiological sinus rhythm is present when the sudden onset criteria is not met, and determines that a pathological rhythm is present when the sudden onset criteria is met.

12. The device of claim 10 wherein the secondary criteria comprises an indication that the patient is exercising.

13. An implantable cardiac stimulation device to provide therapy to a patient's heart, the device comprising:
  a sense amplifier to sense intrinsic signals from the patient's heart and to generate corresponding sense signals;
  a memory circuit to store interval thresholds to determine the type of antiarrhythmic therapy to be applied to the patient's heart for a range of heart rates defined by the interval thresholds;
  a control and timing circuit coupled to the sense amplifier and the memory circuit to generate control signals responsive to the sense signals and the interval thresholds, the control signals to define one of a plurality of antiarrhythmic therapies, wherein the therapy is selected in accordance with the relationship of the sensed heart rate and the interval thresholds;
  an interval threshold adjusting circuit to adjust the interval thresholds stored in the memory circuit in accordance with the response of the patient to the selected antiarrhythmic therapy; and
  a morphology discrimination circuit coupled to the control and timing circuit, at least one of the interval thresholds modified in accordance with a morphology detection applied to the intrinsic signals;
  wherein the interval thresholds define ventricular rate ranges, each range corresponding to a cardiac condition, and wherein the control and timing circuit determines the cardiac condition based at least in part on a ventricular rate corresponding to one of the ranges;
  wherein the control and timing circuit further determines the cardiac condition based on a secondary criteria; and
  wherein the secondary criteria comprises a mean ventricular rate interval ($VRI_M$) within a respective zone.

14. An implantable cardiac stimulation device to provide therapy to a patient's heart, the device comprising:
  a sense amplifier to sense intrinsic signals from the patient's heart and to generate corresponding sense signals;
  a memory circuit to store interval thresholds to determine the type of antiarrhythmic therapy to be applied to the patient's heart for a range of heart rates defined by the interval thresholds;
  a control and timing circuit coupled to the sense amplifier and the memory circuit to generate control signals responsive to the sense signals and the interval thresholds, the control signals to define one of a plurality of antiarrhythmic therapies, wherein the therapy is selected in accordance with the relationship of the sensed heart rate and the interval thresholds;
  an interval threshold adjusting circuit to adjust the interval thresholds stored in the memory circuit in accordance with the response of the patient to the selected antiarrhythmic therapy; and
  a morphology discrimination circuit coupled to the control and timing circuit, at least one of the interval thresholds modified in accordance with a morphology detection applied to the intrinsic signals;
  wherein the interval thresholds define ventricular rate ranges, each range corresponding to a cardiac condition, and wherein the control and timing circuit determines the cardiac condition based at least in part on a ventricular rate corresponding to one of the ranges;
  wherein the control and timing circuit further determines the cardiac condition based on a secondary criteria; and
  wherein the secondary criteria comprises a success rate of converting the patient's rhythm to a normal rhythm.

15. The device of claim 14 wherein the control and timing circuit determines that an interval threshold adjustment is needed when the success rate is low, and determines that an interval threshold adjustment is not needed when the success rate is high.

16. The device of claim 14 wherein the memory circuit additionally stores a plurality of rules, wherein the rate threshold adjusting circuit adjusts the interval threshold using the stored rules.

17. A method for providing therapy to a patient's heart, the method comprising:
  sensing intrinsic signals from the patient's heart and generating corresponding sense signals;
  storing interval thresholds to determine the type of antiarrhythmic therapy to be applied to the patient's heart for a range of heart rates defined by the interval thresholds;
  generating control signals responsive to the sense signals and the interval threshold, the control signals defining one of a plurality of antiarrhythmic therapies, wherein the therapy is selected in accordance with the relationship of the sensed heart rate and the interval thresholds; and
  analyzing success rates of the antiarrhythmic therapies to convert the patient's rhythm to a normal sinus rhythm and adjusting the interval thresholds in accordance with the success rates of the selected antiarrhythmic therapies, at least one of the interval thresholds modified in accordance with a morphology discrimination applied to the intrinsic signals.

18. The method of claim 17 wherein the interval thresholds define a very slow ventricular tachycardia zone, a slow ventricular tachycardia zone, and a fast ventricular tachycardia zone.

19. The method of claim 18 wherein the at least one of the interval thresholds is an interval threshold VT1I, and wherein the morphology discrimination comprises comparing a QRS complex of the intrinsic signals with a stored template to verify the very slow ventricular tachycardia.

20. The method of claim 19 wherein the QRS complex is compared with the stored template when a ventricular rate interval is between 100% and 130% of the interval threshold VT1I.

21. The method of claim 17 further comprising generating therapeutic pulses to the patient's heart in response to the control signals.

22. The method of claim 21 wherein the therapeutic pulses comprises AntiTachycardia Pacing therapy (ATP), and wherein an interval threshold VT1I is increased when the ATP is successful.

23. The method of claim 22 wherein the interval threshold VT1I is increased to ($VRI_M+2\sigma$), wherein $VRI_M$ is the mean ventricular rate interval and $\sigma$ is the standard deviation.

24. The method of claim 21 wherein the interval thresholds define a very slow ventricular tachycardia zone, a slow ventricular tachycardia zone, and a fast ventricular tachycardia zone, and wherein the therapeutic pulses are less aggressive for antitachycardia therapy when the sensed heart rate corresponds to the very slow ventricular tachycardia zone and the slow ventricular tachycardia zone, and the therapeutic pulses are more aggressive for antitachycardia therapy when the sensed heart rate corresponds to the fast ventricular tachycardia zone.

25. The method of claim 24 wherein the interval thresholds define ventricular rate ranges, each range corresponding to a cardiac condition, and wherein determination of the cardiac condition is based on a ventricular rate corresponding to one of the ranges.

26. The method of claim 25 wherein the cardiac condition is based on a secondary criteria.

27. The method of claim 26 wherein the secondary criteria comprises sudden onset, wherein the presence of physiological sinus rhythm is determined when the sudden onset criteria is not met, and wherein the presence of a pathological rhythm is present when the sudden onset criteria is met.

28. The method of claim 26 wherein the secondary criteria comprises an indication that the patient is exercising.

29. The method of claim 26 wherein the secondary criteria comprises a mean ventricular rate interval ($VRI_M$) within a respective zone.

30. The method of claim 26 wherein the interval threshold is adjusted in the direction of the mean ventricular rate interval ($VRI_M$) within a respective zone.

31. The method of claim 17 wherein the patient's heart beats at a ventricular rate and the interval thresholds are related to the ventricular rate of the patient's heart.

32. The method of claim 17 wherein an interval threshold adjustment is needed when the success rate is low, and wherein an interval threshold adjustment is not needed when the success rate is high.

33. The method of claim 17 further comprising storing a plurality of rules, wherein the interval threshold is adjusted using the stored rules.

34. An implantable cardiac stimulation device to generate antitachyarrhythmic therapy for a patient's heart, the device comprising:
a sense amplifier to receive intrinsic signals indicative of ventricular activity and to generate corresponding sense signals;
a condition detector to receive the sense signals and to generate patient condition signals indicative of the condition of the patient based on the sense signals and a set of thresholds;
a threshold level setting circuit to generate the thresholds;
a timing and control circuit to generate command signals based on the patient condition signals and the sense signals, the command signals defining a therapy for the patient corresponding to the patient condition signals;
an output signal generator to receive the commands and to responsively generate therapeutic pulses to revert the patient condition to a sinus state; and
a therapy success detector to analyze the therapeutic pulses to determine a success rate at which the therapeutic pulses have reverted the patient condition to a sinus state, wherein the threshold setting circuit is coupled to the therapy success detector to adjust the thresholds in accordance with the determined success rate;
wherein the threshold setting circuit adjusts at least one of the thresholds in accordance with a morphology discrimination applied to the intrinsic signals.

35. The device of claim 34 wherein the thresholds define a very slow ventricular tachycardia zone, a slow ventricular tachycardia zone, and a fast ventricular tachycardia zone.

36. The device of claim 35 wherein the at least one of the interval thresholds is an interval threshold VT1I, and wherein the morphology detection comprises comparing a QRS complex of the intrinsic signals with a stored template to verify the very slow ventricular tachycardia.

37. The device of claim 36 wherein the QRS complex is compared with the stored template when a ventricular rate interval is between 100% and 130% of the interval threshold VT1I.

38. The device of claim 36 wherein the therapeutic pulses comprises AntiTachycardia Pacing therapy (ATP), and wherein the interval threshold VT1I is increased when the ATP is successful.

39. The device of claim 38 wherein the interval threshold VT1I is increased to ($VRI_M+2\sigma$), wherein $VRI_M$ is the mean ventricular rate interval and $\sigma$ is the standard deviation.

* * * * *